United States Patent [19]

Prater et al.

[11] 4,034,761

[45] July 12, 1977

[54] DISPOSABLE ELECTROSURGICAL SWITCHING ASSEMBLY

[75] Inventors: Earle F. Prater, Long Beach; Frank L. Poole, Sante Fe Springs, both of Calif.

[73] Assignee: The Birtcher Corporation, Los Angeles, Calif.

[21] Appl. No.: 640,739

[22] Filed: Dec. 15, 1975

[51] Int. Cl.² .................. A61B 17/36; A61N 3/06; H01H 9/06; H01H 11/00
[52] U.S. Cl. .................. 128/303.14; 128/303.17; 200/6 C; 200/153 K; 200/157; 29/622; 339/256 SP; 339/258 S
[58] Field of Search .................. 128/303.13, 303.14, 128/303.17, 303.15, 303.18, 405; 339/256 SP, 258 S; 200/157, 6 BA, 6 BB, 6 C, 61.85, 153 K; 29/622

[56] References Cited

U.S. PATENT DOCUMENTS

| 3,511,951 | 2/1970 | Miller | 200/157 |
|---|---|---|---|
| 3,532,095 | 10/1970 | Miller et al. | 128/303.13 |
| 3,691,324 | 9/1972 | Brantingson | 200/6 C X |
| 3,720,896 | 3/1973 | Beierlein | 128/303.13 X |
| 3,801,766 | 4/1974 | Morrison, Jr. | 128/303.14 X |
| 3,807,404 | 4/1974 | Weissman et al. | 128/303.14 |
| 3,875,945 | 4/1975 | Friedman | 128/303.14 |
| 3,911,241 | 10/1975 | Jarrard | 128/303.17 |
| 3,929,137 | 12/1975 | Gonser | 128/303.14 |

FOREIGN PATENT DOCUMENTS

| 811,682 | 4/1937 | France | 128/303.14 |
|---|---|---|---|
| 1,184,311 | 7/1959 | France | 339/258 S |
| 1,166,130 | 10/1969 | United Kingdom | 339/256 SP |

Primary Examiner—Kyle L. Howell
Assistant Examiner—Lee S. Cohen
Attorney, Agent, or Firm—Jackson & Jones

[57] ABSTRACT

A disposable electrosurgical unit for generating electrical signals intended for applications to the body of a patient via an electrosurgical electrode is provided. Cutting signals and coagulation signals can be applied by the actuation of a switch in the handle supporting a removable blade electrode. The electrode blade has a mounting end configuration that can be removably mounted in a receptacle portion of a resilient conductive member. The conductive member is biased by its particular bowed shape and mounting configuration away from wire wrap contacts connected to a power generator source. The switching member is mounted in the electrode handle for selectively moving one of the bowed portions of the resilient conductive member into contact with a wire wrap contact for actuation of the electrode blade in a desired operative mode.

22 Claims, 4 Drawing Figures

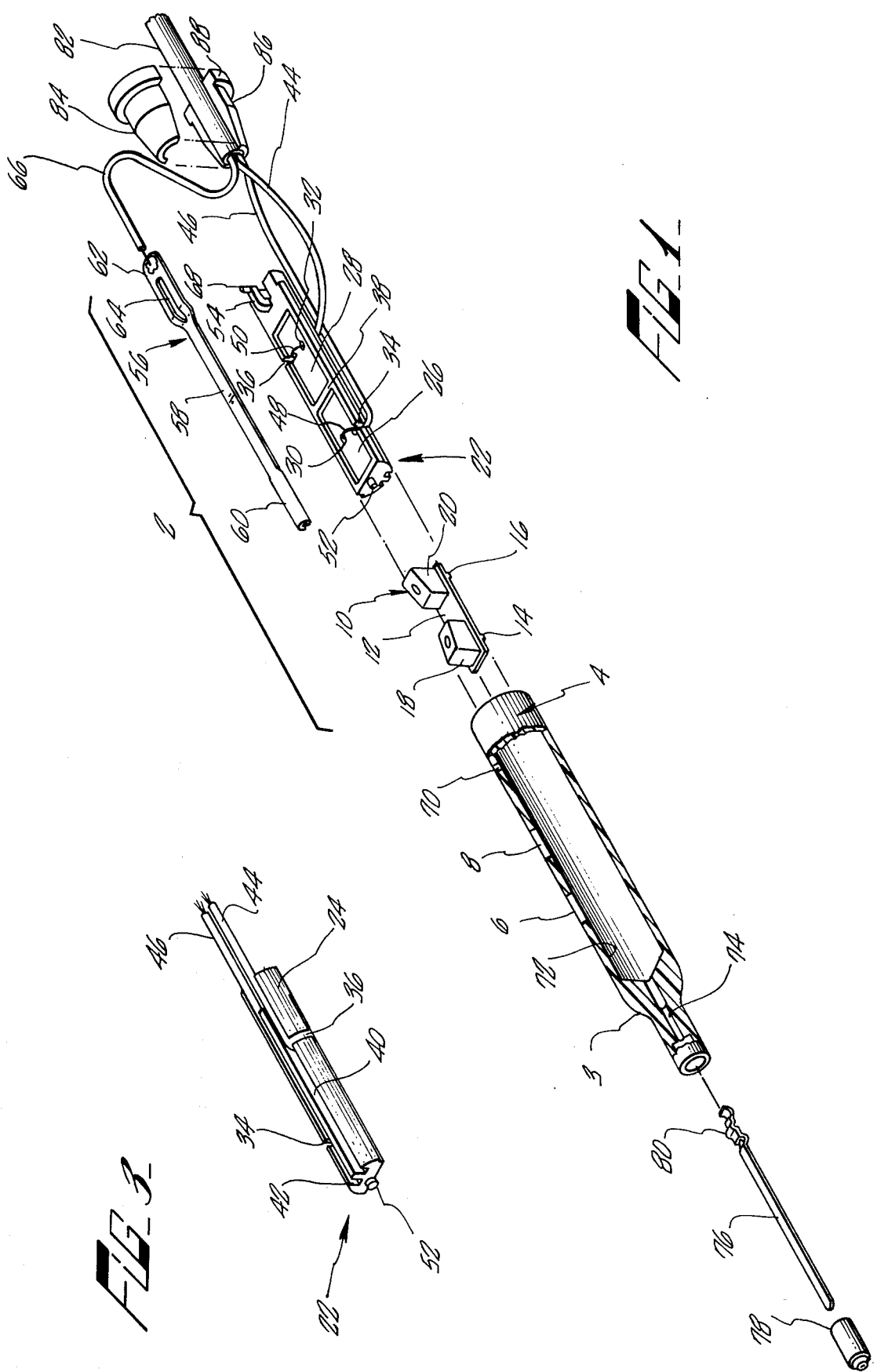

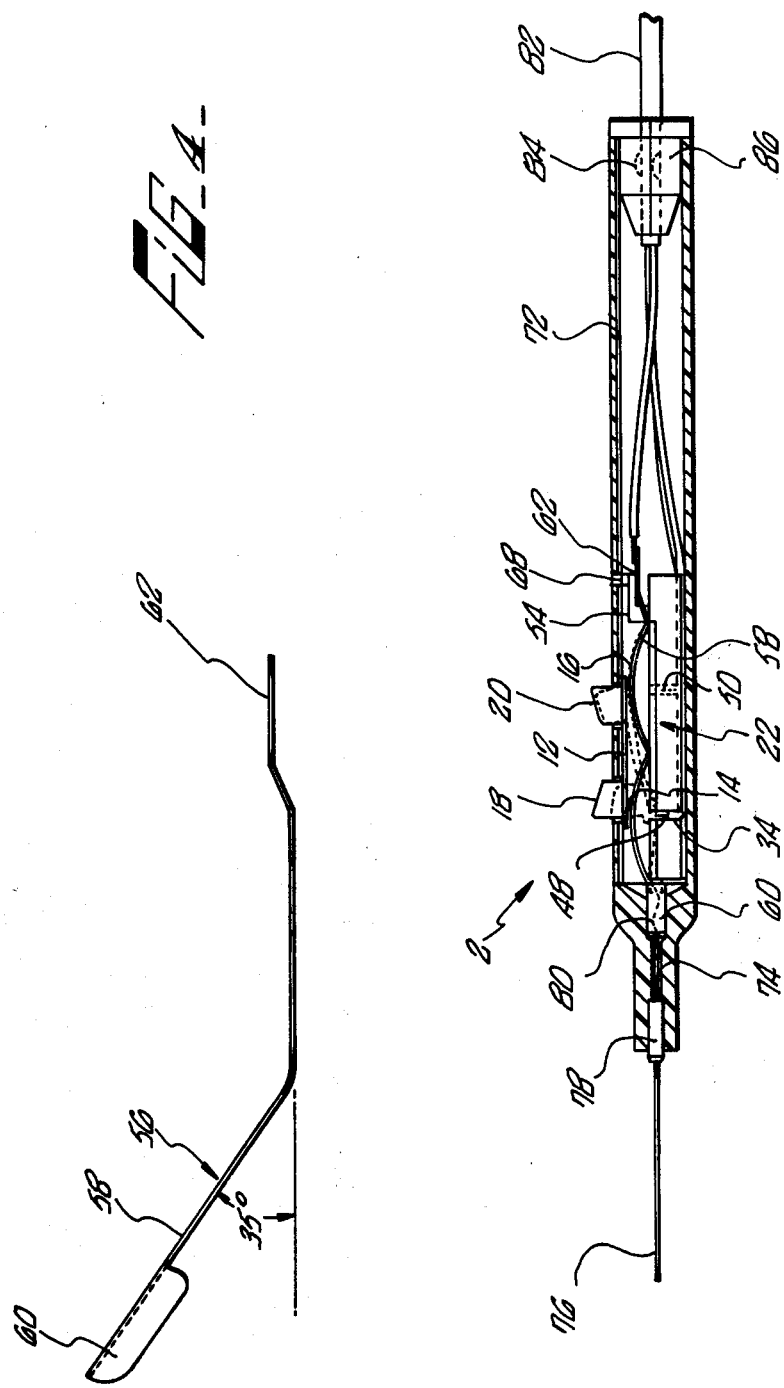

DISPOSABLE ELECTROSURGICAL SWITCHING ASSEMBLY

BACKGROUND OF THE INVENTION

1. Field of the Invention

The present invention relates to diathermic instruments and, more particularly, to a disposable electrosurgical switch handle and a removable electrode blade that is capable of supplying a high frequency current to a patient.

2. Description of the Prior Art

Various forms of diathermic surgical tools have been suggested and utilized in the medical field for a considerable period of time. These instruments have been utilized, for example, to burn or cut tissue. Recently, these instruments have been improved to permit incisions and hemostasis with a minimum disturbance of adjacent tissue. These instruments have utilized radio frequency electrical energy generally in the range of half million cycles per second to over two million cycles per second. Generally, these instruments have utilized three different signals which are characteristically referred to as cutting signals, coagulation or hemostasis signals and a blend of signals or fulgurating signals which combine both the cutting and coagulation signals. These high frequency or radio frequency signals are generally applied to a patient by an electrode and conducted through the patient's body via a ground path provided by an electrode plate or indifferent plate that is maintained in contact with the patient's body. The application of the signals to the patient is through an electrosurgical electrode which applies the high frequency energy to a concisely concentrated point on the patient's body. The relatively large ground electrode plate provides an area for removing the applied energy without affecting the patient.

As is known, the actual cutting is accomplished by the concentrated application of high frequency electrical energy which effectively destroys the body cells directly beneath the electrosurgical electrode. The hemostasis or coagulation energy signals produce coagulation by the dehydrating or shrinking of the blood vessel walls around a contained clot of coagulated blood. This fusion or uniform coagulation of the blood vessel and its contents effectively seals off the flow of blood. Typically, such coagulation signals or pulses of energy have a dampened sinusoidal wave form.

The fulguration or blended signals, formed by combining the cutting and hemostasis signals, can be effectively utilized for accomplishing cutting and coagulation at the same time. Alternating periods of each signal are sometimes utilized to form the blended signals.

The choice of the particular mode of operation of the electrosurgical instrument must frequently be accomplished with a minimum of diversion of the doctor from the site of surgery. In addition, the doctor must be able to maintain his hands on the switching handle that contains the electrosurgical electrode. Finally, it is particularly desirable that the electrosurgical instrument be economically produced, so that it can be disposed after use, thus, insuring a new sterile instrument for each operation.

The Judson U.S. Pat. No. 3,885,569 is cited to disclose an electrosurgical unit for generating electrical signals for an electrosurgical electrode.

The Friedman U.S. Pat. No. 3,875,945 discloses an electrosurgical switching handle that is capable of being operated without a ground plate and utilizes a spring biased wire member for holding the surgical electrode blade. A pressure sensitive two position control switch is located in an area adjacent the patient and may either be foot operated or mounted on the handle approximate to the cutting tip. The doctor, by increasing the pressure of the control switch, is purportedly able to vary the level of output voltage from the power supply.

One commercial switch for an electrosurgical handle contains a centrally pivotable actuator that is capable of overcoming a biased spring contact on either side of the actuator.

The Burger U.S. Pat. No. 2,993,655 discloses a foot operated treadle switch for controlling the mode of operation between cut and coagulate position.

The Anderson U.S. Pat. Nos. 3,683,923 and 3,699,967, Judson U.S. Pat. No. 3,885,565, Gonser U.S. Pat. Nos. 3,804,096; 3,870,047; Jarrard U.S. Pat. No. 3,911,241; and Comerford, et al. U.S. Pat. No. 3,879,592 are cited of general interest.

It is the intention of the subject invention to provide a highly dependable and disposable electrosurgical switching handle that is compatible with the solid state technology that is providing a greater amount of electrical power for electrical surgical purposes.

SUMMARY OF THE INVENTION

The present invention provides an electrosurgical disposable switching handle that is compatible with electrosurgical units for providing cutting and coagulation in the medical field and a method of manufacturing the same. The handle can be molded from plastic and includes a holding member for appropriate connection of wire wrap electrical leads to a power supply capable of generating the desired radio frequency or high frequency electrical signals for cutting and coagulation. An electrically conducting resilient member is connected to the holding member to respectively bow a first and second portion of the resilient member away from the respective coagulation and cutting wire electrical contacts. A switch member can protrude from the handle surface while biased by the respective bow portions of the resilient member. Selective actuation of the switch member can effectuate the power contact between the resilient member and the appropriate electrical contact. The resilient member is slotted at one end to be restrained by a mounting arm while it is shaped into a split tubular configuration at the other end for mounting over a mounting post on the holding member. The split tubular end of the resilient member is adapted to resiliently restrain a removable electrode blade. The base of the electrode blade can be provided with dimpled protrusions for expanding the split tubular portion of the resilient member during the retaining mode. The individual components are designed for a highly dependable utilization while permitting an economical assembly so that the switching handle can be disposable, thus assuring a sterile instrument for each operation.

The present invention both to its organization and manner of operation, together with further objects and advantages thereof, may best be understood by reference to the following description, taken in connection with the accompanying drawings and claims.

BRIEF DESCRIPTION OF THE DRAWINGS

FIG. 1 is a perspective exploded view of the electrosurgical unit of the present invention;

FIG. 2 is a cross-sectional view of an assembled electrosurgical unit of the present invention;

FIG. 3 is a bottom view of the contact mounting member of the present invention; and FIG. 4 is a side view of the elongated contact spring in an unrestrained position.

DESCRIPTION OF THE PREFERRED EMBODIMENT

The following description is provided to enable any person skilled in the art of designing diathermic instruments to make and use the invention and sets forth the best mode contemplated by the inventors of carrying out their invention. Various modifications, however, will remain readily apparent to those skilled in the art, since the generic principles of the present invention have been defined specifically herein to provide an easily manufactured sterile electrosurgical switching handle instrument having component part of a relatively economical nature, so that the instrument is disposable after a single operation on a patient. Thus, the present invention has been optimized to insure the availability of a sterile electrosurgical instrument for every operation.

The eltrosurgical switching handle apparatus of the present invention can removably mount an electrode for applying a high frequency electrical signal to biological tissue. The electrode can be powered from a high frequency generator capable of varying the power amplitude of the electrical signals. The doctor can select the desired frequency signal to provide either a cutting or coagulation operative mode. Various forms of high frequency current generators can be utilized along with various forms of electrode blades. With the electrosurgical instrument, a high frequency current will be applied to the tissue by way of an electrode having a relatively small cross section, so as to obtain a high current density at the operation site. Generally, an indifferent electrode which can take the form of a stainless steel plate is operatively connected to the patient and a conductive fluid can be applied to the patient to increase the contact area. It is highly desirable to provide for use with an electrosurgical unit, a disposable sterile switching handle assembly to minimize the possibility of infection. An example of an electrosurgical unit for generating approximate high frequency current is disclosed in the Judson U.S. Pat. No. 3,885,569, and is incorporated herein by reference to supplement the present disclosure.

Referring to FIG. 1, a perspective exploded view of the disposable electrosurgical switching assembly of the present invention is provided.

The electrosurgical switching handle assembly 2 includes housing 4 which can have any desired configuration. In the preferred embodiment, the housing 4 is of a tubular shape and is opened at both ends. One end of the housing has a reduced neck portion 3 for mounting a removable electrode blade 76 to be discussed subsequently. Preferably, the housing 4 is formed from an injection moldable plastic, such as Delrin, as will be a number of the components to be subsequently described herein. Adjacent the front portion of the housing 4 is a pair of rectangular apertures 6 and 8 adapted to receive a selector member 10. The selector member 10 includes a flat base plate 12 having a pair of transverse ribs 14 and 16 on one side and a pair of elevated step, or button, members 18 and 20 on the other side.

As can be seen from the phantom lines of FIG. 2, the selector member 10 is adapted to be freely mounted in the housing 4 and extend through the apertures 6 and 8 in the housing 4 so that it is accessible from the exterior of the housing 4. Appropriate indicia, such as CUT and COAG can be printed or molded on the exterior of the housing 4 adjacent the protruding buttom members 18 and 20.

A unique electrical contact mounting member 22 can be seen respectively in FIGS. 1 and 3. The mounting member 22 has a half cylindrical body 24 with a pair of indentations, or rectangular, recessed depressions 26 and 28 on the flat surface of the half cylindrical body 24. Other configurations are, of course, operative in the invention besides the cylindrical form. Advantageously, the cylindrical form compliments the internal circular configuration of the tubular housing 4.

Wire holes 30 and 32 extend through the half cylindrical body 24 on the central portion of the respective recessed indentations 26 and 28. Aligned with the respective wire holes are side slots 34 and 36 cut, or molded, into the recessed indentations 26 and 28, respectively. Separating the two recessed indentations 26 and 28 is a bearing rib 38.

Referring specifically to FIG. 3, a pair of longitudinal bottom wire slots 40 and 42 extend the length of the half cylindrical body 24. The respective wire holes 30 and 32 are aligned to open on the respective longitudinal slots 40 and 42, respectively. Likewise, the side slots 34 and 36 extend respectively, into the longitudinal slots 42 and 40, respectively.

Referring to the perspective view shown in FIGS. 1 and 3, a pair of wires 44 and 46 can be appropriately stripped and the exposed metal core inserted into a respective wire hole and wrapped through a respective side slot to extend along the appropriate longitudinal slot throughout the length of the half cylindrical body 24. The resulting exposed wire provide wire wrap electrical contacts, or terminal members, 48 and 50 in approximately the centroid of the respective recessed openings 26 and 28. As can be readily appreciated, other forms of electrical contacts on the recessed openings 26 and 28 can be used such as rivet heads, screw heads, etc., and accordingly, the present invention should not be limited to the wire wrap contacts 48 and 50.

Projecting from the forward end of the half cylindrical body 24 is a cylindrical mounting post 52, while projecting from adjacent the rear end of the half cylindrical body 24 is an upwardly projecting cantilevered alignment and contact base member 54. Adapted to be mounted on the respective mounting post 52 and over the contact base member 54 is an elongated resilient member 56 that can be best seen in FIGS. 1 and 4. Resilient member 56 can be made from an electrically conducting material such as beryllium copper that can be cold formed and heat treated to provide a predetermined amount of bend, or curvature, e.g. 35°, in the middle of the central ribbon portion 58 that extends between the split tubular portion 60 and the contact plate 62. Thus, the resilient member 56 has a V-like shape when in an unrestrained position. The contact plate 62 further has an elongated slot 64 that permits the contact plate portion 62 to be mounted over the contact base member 54 to permit a subsequent mounting of the split tubular portion 60 onto the mounting post 52. While in the preferred embodiment the resilient member 56 is made from an electrically conductive material, it is possible to utilize other forms of non-conductive resilient or overcenter bias material and attached thereto, an appropriate electrically conductive but passive material.

The bend in the center of the band, or ribbon portion 58, is aligned by the mounting of the resilient member 56 with the bearing rib 38 on the mounting member 22. As a result of this mounting and the coaction with the bearing rib 38, the elongated resilient member 56 is bowed into a first and second part of the ribbon portion 58 away from respectively the wire wrap contents 48 and 50. Rib 38 prevents the resilient member from touching both contacts 48 and 50 at the same time in case both the CUT and COAG button members are pushed simultaneously.

The contact plate 62 can be electrically connected, for example, by solder to an electrical wire 66.

The contact base member 54, beside serving as an attachment point for the elongated resilient member 56, serves an additional alignment function for positioning the mounting member 22 in the housing 4. An indexing pin 68 on the member 54 is designed to snap into an indexing hole 70 in the housing 4. The cantilevered configuration of the contact base member 54 along with the resiliency of the molded plastic of the half cylindrical body 24 provides a limited amount of movement to the indexing pin 68. An alignment slot 72 extends along the interior of the tubular housing 4 an serves as a guide for the mounting of the contact member 22. The indexing pin 68 slides along the alignment slot 72 in a state of tension until it can be released by engagement with the indexing hole 70. Thus, automatic indexing means are provided for fastening the mounting member 22 and switch, or selector member, 10 in the housing 4.

The front portion of the housing 4 has a recessed neck configuration 3 with a variable diameter bore 74. The interior portion of the bore 74 is sized to receive the split tubular portion 60 of the elongated resilient member 56. The outer end of the bore 74 is enlarged to receive a stop, or alignment, member 78 mounted on an electrode blade 76.

The electrode blade 76 is generally formed from stainless steel and has been specifically designed to provide a dimpled protrusion configuration 80 at one end that is dimensioned to coact with the split tubular portion 60 of the elongated resilient member 56 to provide a removable electrode blade 76 configuration. The specific configurations of the dimpled protrusions 80 can be varied while still effectuating a removable electrical connection. In the embodiment disclosed, the dimpled protrusion configurations 80 are of a circular dimpled shape that can be of alternative convex and concave configurations pressed into the stock or blank of the electrode blade. The circular shape allows for rotation of the electrode blade 76 by the doctor for any desired position relative to the button members 18 and 20. Mounted on the electrode blade 76 is a stop member 78 which regulates the insertion limit of the electrode blade 76 into the housing 4 and into the split tubular portion 60 of the resilient member 56. The stop member 78 can be a plastic plug or a bent configuration of the blade 76 itself. For purposes of the present invention, the dimpled protrusion configuration 80 can be broadly identified as a sinusoidal connecting portion and should not be limited to a dimpled configuration, since triangular, rectangular or other configurations could be utilized.

The individual wires 44, 46 and 66 can be covered with a sheath 82 and locked to the end of the housing 4 by a pair of half cylindrical plug members 84 and 86. The exterior of the cylindrical plug members 84 and 86 have a tapered configuration which terminates in a stop flange 88. Both of the half cylindrical plug members 84 and 86 are brought together to form a plug with a central bore. One half cylindrical plug member has a transverse rib (not shown) in its bore section coacting with a recessed indentation (not shown) in the other half plug member to permit a crimping action to be applied to the sheath 82 as the cylindrical plug members are appropriately inserted into the housing 4.

During assembly, the selector, or button, member 10 is inserted into the tubular housing 4 and positioned within the respective apertures 6 and 8. The base plate 12 limits the exterior protrusion of the individual push button, or step, members 18 and 20.

The electrical contact mounting member 22 is appropriately wire wrapped to provide wire wrap contacts 48 and 50 in the center of the recessed openings 26 and 28. The wires are also appropriately aligned into the longitudinal slots 40 and 42 and may be fastened or adhered directly to the half cylindrical body 24 is desired. With the wires positioned in the appropriate slots 40 and 42 the outside configuration of the half cylindrical body 24 complements the interior configuration of the tubular housing 4.

The elongated resilient member 56 has been prestressed and heat treated to provide the desired V shape bent configuration in an unrestrained state. Wire 66 can be appropriately secured to the elongated resilient member 56 either after or before its mounting on the half cylindrical body 24. The contact plate 62 of the slot 64 is positioned over the contact base member 54 and the entire resilient member 56 is slid forward to provide ample room for the mounting of the split tubular portion 60 onto the mounting post 52 on the front end of the half cylindrical body 24. With the subsequent rearward movement of the elongated resilient member 56, which is permitted by the slot 64, the curved or bent portion is aligned with the bearing rib 38. In this configuration, a first and second portion of the resilient member 56 is bowed upward and away from the respective wire wrap contacts 48 and 50.

With the button member 10 held in an extended position out of the housing 4, an appropriate tool can be utilized to push the electrical contact mounting member 22 into its desired position within the housing 4. The indexing pin 68 on the contact base member 54 is appropriately aligned with the longitudinal alignment slot 72 extending along the interior of the tubular housing 4. The cantilevered contact base member 54 is resilient enough to permit the bending of the index pin 68 as the contact mounting member is slid into the housing 4 underneath the selector member 10. The indexing pin 68 snaps upward and coacts with the indexing hole 70 in the housing 4 to lock the contact mounting member 22 into position with the front of the half cylindrical body 24 seated against the recessed neck portion of the housing 4.

The respective first and second bowed portions of the elongated resilient member 56 are biased upward to contact the selector button member respectively adjacent the traverse ribs 14 and 16. Thus, the selector member is maintained in the housing 4 by the resilient bias of the resilient member 56. The inward movement of a respective step member or button portion causes the transverse rib and the edge of the base plate 12 to depress or bend the bowed portion of the resilient member 56 downward into an electrical contact with the appropriate wire wrap contact positioned beneath the bowed portion of the resilient member. This completes the electric circuit and permits the application of a high frequency electrical signal through the resilient member 56 to the electrode 76 that is mounted from the exterior of the housing 4 into the split tubular portion 60.

While the switch mechanism of the present invention is applicable in other environments, it is of particular value in an electrosurgical switch handle to provide a highly reliable but economical mechanism. The switching function of the selector 10 is accomplished with a low voltage milliamp current flow through the wire wrap contacts 48 or 50 and member 58. Thus, any sparking as a result of a high voltage across the open contact of member 58 and wire contacts 48 or 50 is prevented. The high voltage - high frequency current is always passed directly through wire 66 to the electrode blade 76.

The actual switching logic (not shown) can, for example use the respective wire wrap contact lines 44 and 46 to short out a high frequency transformer circuit which in turn provides an enabling signal that the switch is closed. The rectified enabling signal can be processed, for example, as a gating signal to a CMOS gate to provide a final logic signal for applying the desired high frequency current to the electrode blade 76 through wire 66.

The switching mechanism of the present invention provides two modes of operation which are appropriately identified on the exterior of the housing 4 with the indicia, CUT and COAG. Mounted on the electrosurgical instrument monitor is an additional switch that is capable of modulating or blending the applied electrical signal. For example, it is highly desirable to provide an optional fulguration mode of operation for the CUT button, wherein a combination of cutting and coagulation will occur when the CUT button is depressed. Accordingly, the additional switch would be actuated to provide the fulgurate frequency signal for the CUT button.

As can be appreciated, the manufacturing of the switching assembly from plastic components and the economical manner of assembly permits the instrument to be disposed after a single use, while at the same time, the unique construction of the individual components insures a highly reliable and precise instrument. Thus, the present invention provides a disposable electrosurgical instrument that assures a sterile instrument for each operation.

As known in the art, the electrosurgical disposable switching handle of the present invention, can be packaged in a sealed envelope. The electrical surgical switching assembly can be provided with the cord in a sterile package and autoclavable and reusable adaptor plugs can then be connected to the cord for connection to an appropriate electrosurgical equipment, such as a solid state electrosurgical unit.

It should be readily appreciated that variations of the present invention can be readily accomplished by those skilled in the art in accordance with the teachings herein and accordingly the scope of the present invention should be measured solely from the following claims, in which I claim.

What is claimed is:

1. An electrosurgical instrument for selectively providing electrical energy to an electrode blade for cutting, coagulation and the like, comprising:
    a housing;
    a selector member movably mounted relative to the housing;
    at least a first and second electrical contact mounted within the housing and adapted to being connected to electrical energy; and
    a resilient member mounted within the housing and extending between the selector member and the first and second electrical contacts, the resilient member including means for conducting electricity and further including electrode blade mounting means at one end for connection to the electrode blade, the electrode blade mounting means being electrically connected to the means for conducting electricity, the selector member operatively moving the resilient member as desired by an operator to electrically interconnect the electrode blade, the means for conducting electricity and one of the first and second electrical contacts.

2. The invention of claim 1 wherein the electrode blade mounting means includes a split tubular end of the resilient member.

3. The invention of claim 1 wherein the resilient member has a V-like shape when in an unrestrained position.

4. The invention of claim 1 wherein the housing has at least a pair of apertures and the selector member has a pair of buttons extending outward of the housing through a respective aperture, the selector member held in the pair of apertures only by the bias of the resilient member.

5. The invention of claim 1 further including mounting means for the resilient member having:
    a mounting post at one end of the mounting means and a protruding contact base member at the other end, the resilient member attached respectively to the mounting post and the contact base member and biasing a first and second portion of the resilient member away from the electrical contacts.

6. The invention of claim 5 wherein the first and second electrical contact are formed by a first and second wire member, the mounting means having a first and second wire wrap slot holding the respective wire members adjacent the resilient member.

7. The invention of claim 6 wherein the housing has at least a pair of apertures and the selector member has a pair of buttons extending outward of the housing through a respective aperture, the selector member held in the pair of apertures only by the bias of the resilient member.

8. The invention of claim 6 wherein the material of the resilient member is selected from an electrically conductive material and further has an elongated slot cooperating with the contact base member of the mounting means.

9. The invention of claim 6 wherein the mounting means has a pair of longitudinal slots receiving the first and second wire members as they extend along the longitudinal direction of the housing.

10. The invention of claim 5 wherein the housing further has an indexing aperture locking the mounting means in the housing.

11. An electrosurgical instrument for selectively providing electrical energy to an electrode blade for cutting, coagulation and the like, comprising:
   a housing;
   means on the housing for holding the electrode blade;
   a selector member movably mounted relative to the housing;
   an electrical contact mounting member positioned within the housing adjacent the selector member and including a mounting post and a protruding contact base member;
   at least a first and second electrical contact mounted on the mounting member for transmitting electrical power to the electrode blade, and
   an electrically conductive resilient member attached to the mounting post and the protruding contact base member to bias a first and second intermediate portion of the resilient member away from the respective first and second electrical contacts, the selector member having means for moving either one of the first and second portions of the resilient member to electrically contact one of the respective electrical contacts.

12. The invention of claim 11 wherein the resilient member further includes electrode blade mounting means for connection to the electrode blade.

13. The invention of claim 12 wherein the electrode blade mounting means includes a split tubular end of the resilient member.

14. The invention of claim 11 wherein the protruding contact base member has an indexing pin and the housing further has an indexing aperture locking the electrical contact mounting member in the housing by the coaction of the indexing pin and the indexing aperture.

15. The invention of claim 11 wherein the resilient member is a one piece blank of conductive metal and has a tubular barrel at one end for receiving the electrode blade and a flat contact plate at the other end.

16. A disposable electrosurgical instrument for selectively providing electrical energy to an electrode blade for cutting, coagulation and the like, comprising:
   a housing;
   a selector member movably mounted relative to the housing;
   an electrical contact mounting member positioned within the housing adjacent the selector member;
   at least a first and second electrical contact mounted on the mounting member;
   a resilient member extending between the selector member and the electrical contact mounting member and biasing the selector member away from the electrical contacts, the resilient member being a one piece blank of conductive metal having a tubular configuration at one end for receiving the electrode blade and an electrical contact plate at the other end for transmitting electrical energy, and
   mounting means for restraining the resilient member to respectively bias a first and second portion of the resilient member away from respectively the first and second electrical contacts, the selector member having means for moving either one of the first and second portions of the resilient member to operatively contact one of the respective electrical contacts.

17. The invention of claim 16 wherein the mounting means includes a mounting post at one end of the electrical contact mounting member and a protruding contact base member at the other end, the resilient member attached respectively to the mounting post and the contact base member and biasing the first and second portion of the resilient member away from the electrical contacts.

18. A switch assembly adapted to being connected to an electrode blade and electrically connected to a variable source of power comprising:
   a housing;
   a selector member movably mounted relative to the housing and having means for providing at least two modes of power connections;
   electrical contact mounting means mounted within the housing adjacent the selector member for providing a connection to the modes of power; and
   a resilient member extending between the electrical contact mounting means and the selector member, the selector member when actuated for a first mode of operation moving a first portion of the resilient member to provide a first power connection with the electrical contact mounting means and when actuated for a second mode of operation moving a second portion of the resilient member to provide a second power connection with the electrical contact mounting means, the resilient member is a one piece blank of conductive metal having an integral electrode blade mounting member at one end.

19. The invention of claim 18 wherein the resilient member is an elongated member contacting the mounting means is a non-current carrying position at three points.

20. The invention of claim 19 wherein the electrical contact mounting means includes a pair of electrical contacts and the resilient member has a pair of bowed portions respectively biased away from a respective electrical contact.

21. A method of manufacturing an electrosurgical instrument switch mechanism having a hollow housing with an alignment groove and aperture indent, an electrical contact mounting member with an indexing member, a selector member, an electrode blade holder and a resilient member comprising the steps of:
   inserting the selector member into the housing;
   connecting the resilient member to extend beyond one end of the electrical contact mounting member to form the electrode blade holder;
   positioning the mounting member with its indexing member in the alignment groove of the housing;
   sliding the mounting member adjacent the selector member until the resilient member operatively biases the selector member and the indexing member coacts with the housing aperture indent to be visible from the exterior of the housing for restraining the mounting member in the housing.

22. A method of manufacturing an electrosurgical instrument switch mechanism for energizing an electrode blade having a hollow housing, an electrical contact mounting member having a pair of terminal contacts, a resilient conductive member and a selector member, comprising the steps of:
   bending the resilient conductive member to form an electrode blade holder;
   inserting the selector member into the housing;
   fastening the resilient conductive member to the mounting member to provide a pair of bowed portions respectively biased away from a respective terminal contact; and
   positioning the mounting member in the housing relative to the selector member to permit a selective forcing of the respective bowed portions by the selector member against a terminal contact for a desired mode of energization of the electrosurgical instrument.

* * * * *

UNITED STATES PATENT AND TRADEMARK OFFICE
CERTIFICATE OF CORRECTION

PATENT NO. : 4,034,761
DATED : July 12, 1977
INVENTOR(S) : EARLE F. PRATER ET AL It is certified that error appears in the above–identified patent and that said Letters Patent are hereby corrected as shown below:

Col. 6, line 27 after 24 delete "is" and insert --if--.

Signed and Sealed this

Eleventh Day of October 1977

[SEAL]

Attest:

RUTH C. MASON
Attesting Officer

LUTRELLE F. PARKER
Acting Commissioner of Patents and Trademarks